United States Patent [19]

Kuraoka

[11] Patent Number: 4,708,777
[45] Date of Patent: Nov. 24, 1987

[54] METHOD AND APPARATUS FOR CONTROLLING HEATER OF A GAS SENSOR

[75] Inventor: Hiroaki Kuraoka, Oobu, Japan

[73] Assignee: Nippondenso Co., Ltd., Kariya, Japan

[21] Appl. No.: 698,546

[22] Filed: Feb. 5, 1985

[30] Foreign Application Priority Data

Feb. 6, 1984 [JP] Japan ................................. 59-20341
Feb. 6, 1984 [JP] Japan ................................. 59-20342

[51] Int. Cl.$^4$ ............................................. G01N 27/46
[52] U.S. Cl. ..................................... 204/1 T; 60/276;
123/440; 204/408; 204/421; 204/424
[58] Field of Search ........................ 204/1 S, 421-429;
60/276, 285; 123/440, 489; 219/482

[56] References Cited

U.S. PATENT DOCUMENTS

| | | | |
|---|---|---|---|
| 4,224,913 | 9/1980 | Barnard ................................ | 123/440 |
| 4,291,572 | 9/1981 | Maurer et al. ...................... | 204/276 |
| 4,332,225 | 6/1982 | Cox et al. ............................ | 204/424 |
| 4,359,030 | 11/1982 | Sone et al. .......................... | 204/425 |
| 4,365,604 | 12/1982 | Sone ..................................... | 204/424 |
| 4,419,190 | 12/1983 | Dietz et al. ......................... | 204/425 |
| 4,430,191 | 2/1984 | Sone et al. .......................... | 204/427 |
| 4,464,244 | 8/1984 | Uchida et al. ...................... | 204/424 |
| 4,472,262 | 9/1984 | Kondo et al. ....................... | 204/425 |
| 4,495,919 | 1/1985 | Daniel et al. ....................... | 123/489 |
| 4,495,922 | 1/1985 | Fujimura et al. .................... | 123/440 |
| 4,538,575 | 9/1985 | Chujo et al. ........................ | 204/424 |

FOREIGN PATENT DOCUMENTS 52-46890 4/1977 Japan .
54-20149 7/1979 Japan .
57-140539 8/1982 Japan .

Primary Examiner—T. Tung
Attorney, Agent, or Firm—Cushman, Darby & Cushman

[57] ABSTRACT

Energization of a heater built in a gas sensor, such as an oxygen sensor, used in an air/fuel ratio control system of an internal combustion engine, is controlled to maintain the temperature of the same within a desired range. The temperature of the heater is calculated using a measured resistance value of the heater, and engine parameters used for estimating a specific engine operating condition. To this end operating state of the engine is first detected to determine whether it is possible to estimate the actual temperature of the heater, and when possible, a reference resistance value of the heater at a reference temperature such as 0° K. or 0° C. is caluclated using estimated heater temperature and a measured resistance value. Once the initial resistance value is obtained, this is used to calculate actual heater temperature using measured resistance value and a predetermined temperature coefficient.

14 Claims, 7 Drawing Figures

METHOD AND APPARATUS FOR CONTROLLING HEATER OF A GAS SENSOR

BACKGROUND OF THE INVENTION

This application pertains to the same general subject matter as co-pending applications, Ser. No. 585,861 filed Mar. 2, 1984 now U.S. Pat. No. 4,543,176, by Hara et al, and Ser. No. 623,219 filed June 21, 1984 now U.S. Pat. No. 4,548,179 by Ninomiya et al but the specific subject matter taught and and claimed is different therefrom.

This invention relates generally to an air/fuel ratio contol system for an internal combustion engine used for motor vehicles or the like, and particularyly, to apparatus for heating an oxygen sensor used for detecting the concentration of oxygen in exhaust gases.

In a typical air/fuel ratio control system used for internal combustion engines of motor vehicles of the type using a three-way catalytic converter, an oxygen sensor is used to detect the concentration of residual oxygen included in exhausted gases from the engine so as to control the air/fuel ratio to be close to a stoichiometric value. Such oxygen sensors have a given operating temperature range in which a detection current corresponding to the concentration of oxygen can be obtained, and in order to keep the temperature of such a sensor at a high value, such as above 500° C., a plutinum heater is built therein to continuously heat the body of the sensor during operation.

However, since the heater is continuously energized to heat the sensor, in the case that the sensor and the heater buit therein are overheated to a temperture such as above 1,400° C. due to abnormal overheating of the exhaust gases, breaking of the heater wire is apt to occur to stop normal detecting operation. Abnormal state of the oxygen sensor may cause the air/fuel ratio control system to supply the engine with an excessively lean mixture. To prevent such undesirable phenemenon therefore, feedback control using the oxygen sensor output is terminated on such abnormal condition and the air/fuel ratio is controlled to a setting value by way of an open loop control as described in Japanese Patent Provisional Publication No. 57-140539. Although this technique of switching from feedback control to open loop control avoids extremely undesired control of an air/fuel mixture, it does not provide a basic solution since the feedback control cannot be recovered unless the broken sensor is replaced with a normal one or repaired.

SUMMARY OF THE INVENTION

The present invention has been developed in order to remove the above-described drawbacks inherent to the conventional air/fuel ratio control system using an oxygen sensor.

It is, therefore, an object of the present invention to provide a new and useful apparatus for controlling heater of an oxygen sensor used in such an air/fuel ratio control system of an internal combustion engine.

According to a feature of the present invention heater energization is controlled by detecting the temperature of the heater of the oxygen sensor provided within an exhaust pipe to prevent overheating, while the heater temperature is calculated using a measured resistance value of the heater, and engine parameters used for estimating a specific engine operating condition. More particulary, operating state of the engine is first detected to determine whether it is possible to estimate the actual temperature of the heater, and when possible, a reference resistance, such as an initial resistance value of the heater at absolute zeropoint is calculated using estimated heater temperature, a known temperature coefficient, and a measured resistance value. Once the initial resistance value is obtained, this is used to calculate actual heater temperature using measured resitance value and the predetermined temperature coefficient.

In accordance with the present invention there is provided apparatus for controlling a heater of a gas sensor used for detecting the concentration of a gas component of exhaust gases from an internal combustion engine, comprising: a temperature sensor for detecting a temperature relating to said engine; first means for detecting a particular engine operating condition from which it is possible to estimate the temperature of said heater using said temperature relating to said engine; second means for measuring an actual resistance value of said heater; third means for calculating a reference resistance value of said heater at a predetermined reference temperature; for calculating the temperature of said heater using said meaured resistance value, said reference resistance value, and a predetermined temperature coefficient; and for producing a control signal using the calculated heater temperature; and fourth means for controlling the energization of said heater in accordance with said control signal.

In accordance with the present invention there is also provided a method of controlling a heater of a gas sensor used for detecting the concentration of a gas component of exhaust gases from an internal combustion engine, comprising the steps of: detecting a temperature relating to said engine; detecting a particular engine operating condition from which it is possible to estimate the temperature of said heater using said temperature relating to said engine; measuring an actual resistance value of said heater; calculating a reference resistance value of said heater at a predetermined reference temperature; calculating the temperature of said heater using said meaured resistance value, said reference resistance value, and a predetermined temperature coefficient; producing a control signal using the calculated heater temperature; and controlling the energization of said heater in accordance with said control signal.

BRIEF DESCRIPTION OF THE DRAWINGS

The object and features of the present invention will become more readily apparent from the following detailed description of the preferred embodiments taken in conjunction with the accompanying drawings in which.

The same or corresponding elements and parts are designated at like reference numerals throughout the drawings.

DETAILED DESCRIPTION OF THE INVENTION

Figure 1:
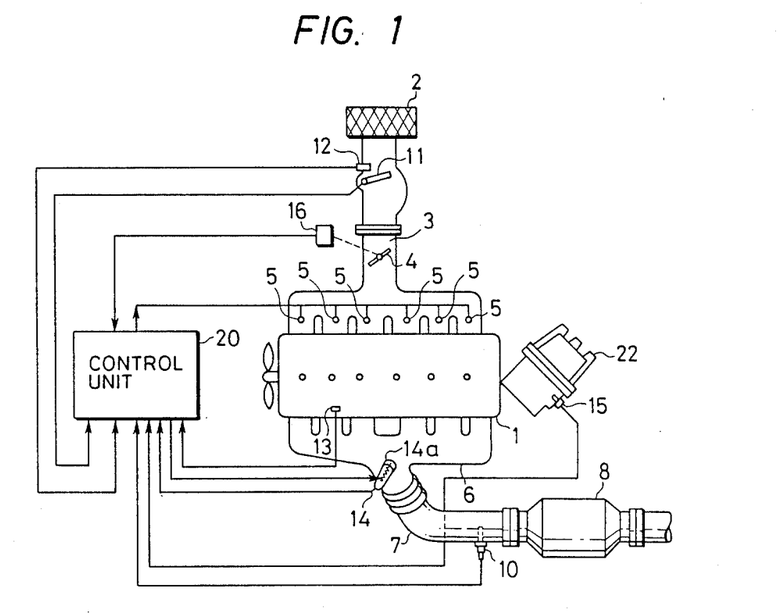
FIG. 1 is a schematic view of the apparatus acccording to the present invention for controlling a heater of an oxygen sensor used in an air/fuel ratio control system.

Referring to FIG. 1, a schematic illustration of an air/fuel ratio control system for an internal combustion engine is shown. The reference 1 indicates a well-known six-cylinder spark ignition internal combustion engine arranged to suck intake air via an air cleaner 2, an intake pipe 3, a throttle valve 4 and an intake manifold into its cylinders. The reference 6 is an exhaust manifold for leading exhaust gases via an exhaust pipe 7 to a catalytic converter 8 and exhausting the same to atomosphere. An airflow meter or sensor 11 of potentiometer type arranged to output an analog voltage indicative of the quantity of intake air is installed in the intake pipe 3. In addition, an intake air temperature sensor 12 of thermister type for detecting the temperature Ta of the intake air and for producing an analog voltage indicative of the temperature of the intake air is also installed in the intake pipe 3. A coolant sensor 13 of thermister type for detecting the temperature Tc of the engine coolant and for producing an analog voltage indicative of the same is installed in the engine body 1. An oxygen sensor 14 for detecting the concentration of residutal oxygen in the exhaust gases and producing an analog voltage porportional to the concentration thereof is provided within the exhaust manifold 6. The oxygen sensor 14 is of solid electrolyte type using principle of concentration cell to detect the concentration of oxygen. More particularly, a platinum heater 14a is built in the oxygen sensor 14 to activate the sensor 14 with a solid electrolyte using zirconium being heated to be over approximately 500° C. irrespective of the operating condition of the engine 1. The platinum heater 14a has a substantially constant positive temperature coefficient a with respect to its temperature, and its resistance value RH is given by:

RH=RHo+αTH wherein

RHo is a resistance value at absolute zeropoint (0° K.), which will be referred to as an initial resistance value hereinater; and TH is a present temperature (° K) of the heater 14a.

As RHo may be used a resistance value at 0° C., and in such a case, the temperature TH is given as having unit of ° C. In this way RHo may be a reference resistance value at any reference temperature, and TH may be the temperature difference between actual temperature of the heater 14 and the reference temperature.

Figure 2:
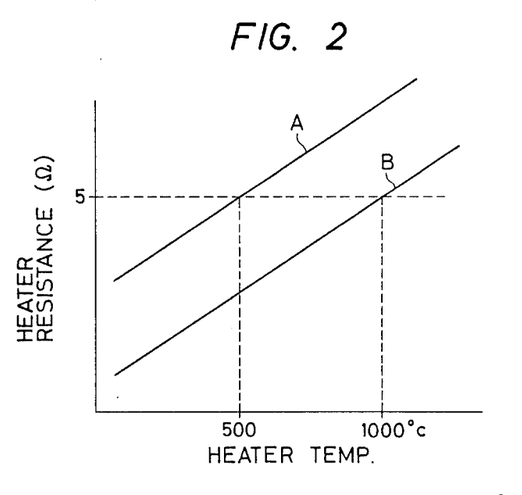
FIG. 2 is a graph showing the relationship between the temperature and resitance value of two like oxygen sensor heaters.

FIG. 2 is a graph showing the relationsip between the temperature of the heater 14a and the resistance value RH. As will be understood from typical two curves in FIG. 2, the initial resistance value RHo varies throughout products due to monuniformity in manufacturing process or the like. For instance, in the case of a heater indicated by a curve A, the resistance RH is 5 ohms at 500° C., whereas the temperature, at which the resistance RH of another heater indicated by a curve B assumes 5 ohms, is 1,000° C. Such variation or scattering throughout products may cause inaccurate measurement of the resistance value of the heater 14a which may lead to inaccurate measurement of the temperature of the heater 14a. In order to avoid such inaccuracy, therefore, the temperature of the heater 14a is first estimated using engine operating condition as will be described hereinlater, and then a resistance value RH of the heater 14a at a reference temperature, such as absolute zeropoint (0° K.)or 0° C., is calculated. Once such a reference resistance value, which may be the above-mentioned initial resistance value RHo at absolute zeropoint, is obtained, then present temperature TH of the heater 14a can be calculated using measured resistance value RH and the predetermined temperature coefficient α.

Turning back to FIG. 1, the reference 10 is a thermister type exhaust gas temperature sensor installed within the exhaust pipe 7, and the reference 16 is a throttle opening degree sensor for detecting the opening degree of the throttle valve 4. The reference 15 is an engine rotational speed sensor of pickup coil type for detecting the rotational speed (rpm) of the crankshaft of the engine 1. This rotational speed sensor 15 is installed within a distributor 22 to face a rotor (not shown) thereof so as to produce a pulse train signal corresponding to engine rpm.

A control unit 20, which may be actualized by a microcomputer and peripheral circuits, is provided to receive detection signals from the above-mentioned various sensors 10 to 16, and to control the amount of fuel supplied to the engine 1. In this embodiment, electromagnetic fuel injection valves 5 are controlled such that their opening duration corresponds to a desired amount of fuel to be injected into respective cylinders. In addition to the air/fuel ratio control, the energization of the heater 14a of the oxygen sensor 14 is also controlled by the control unit 20. This control unit 20 will be further described in detail with reference to FIG. 3.

Figure 3:
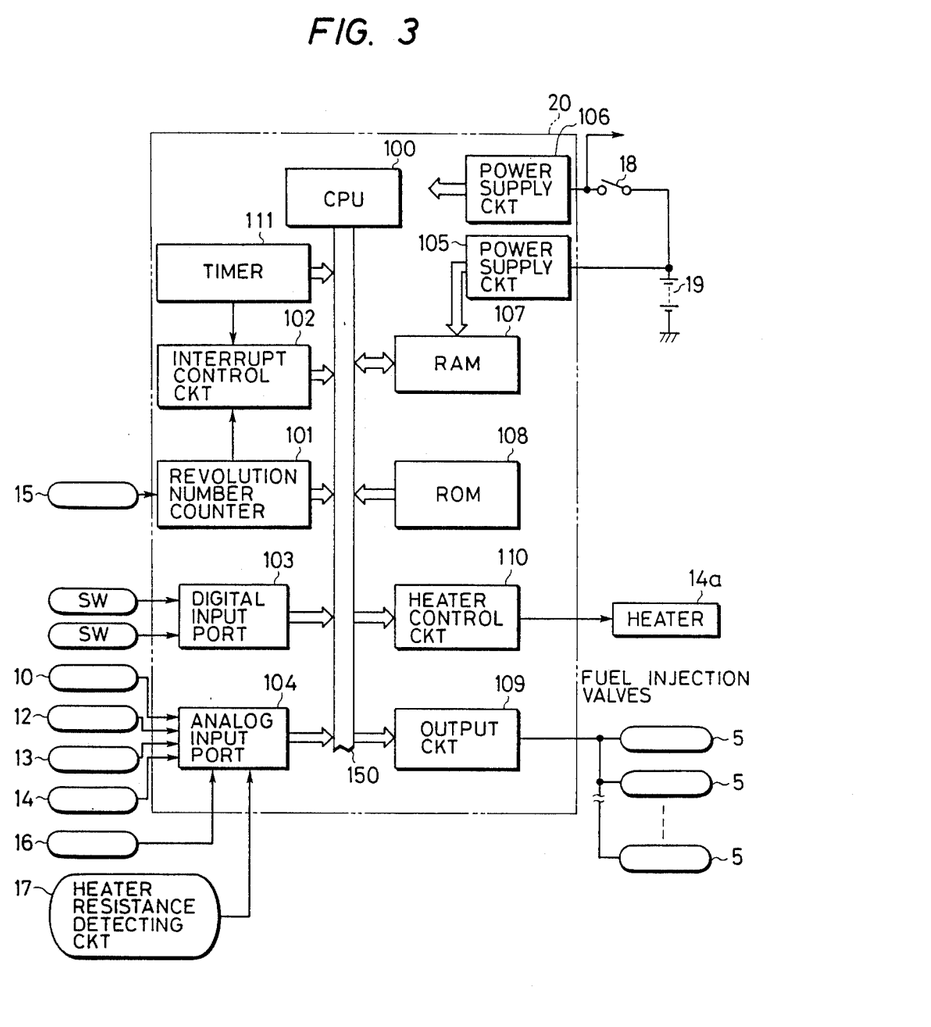
FIG. 3 is a schematic block diagram of the appratus according to the present invention.

Referring now to FIG. 3, the control unit 20 comprises a central processing unit (CPU) 100, several memories and various peripheral or auxiliary circuits so that fuel injection amount and energizing duration of the heater 14a are computed in accordance with a predetermined program. The CPU 100 per se is well known, and one of 8, 12 or 16 bit type may be used.

A revolution number counter 101 is provided for counting the number of pulses from the electromagnetic pickup 37 so that data Ne indicative of engine speed is fed to the CPU 100. The revolution number counter 101 also has a function of generating an interrupt command signal in synchronism with the engine rotation. The interrupt command signal is fed to an interrupt control circuit 102 which sends an interrupt request via a bus 150 to the CPU 100.

A digital input port 103 is provided to receive signals from an airconditioner switch and a starter switch and to send them to the CPU 100.

An analog input port 104 comprises an A/D converter, a multplexer or the like for receiving signals from various sensors and transmitting the same via the bus 150 to the CPU 100. In detail, various detection signals from the intake airflow sensor 1, the intake air temperature sensor 12, the coolant temperature sensor 13, the exhaust gas temperature sensor 10, the oxygen sensor 14, the throttle valve opening degree sensor 16 are all A/D converted to be transmitted in sequence to the CPU 100.

Power supply circuits 105 and 106 are provided for regulating an output voltage from a vehicle-mounted battery 19. The first power supply circuit 106 is connected via a key switch 18 to the battery 19, while the second power supply circuit 105 is directely connected to the battery 19. The second power supply circuit 105 is arranged to supply a random-access-memory (RAM) 107 with power all the time, and the first power supply circuit 106 is arranged to supply remaining circuits with power when the key switch 18 is in on stae.

The RAM 107 is used to temporarily store various data so that the CPU 100 executes programs as will be described later. Since the RAM 107 always receives power irrespective of the state of the key switch 18, the contents stored therein are prevented from being erased. In other words, the RAM 107 functions as a nonvolatile memory of power backup type.

A read-only-memory (ROM) 108 is provided to store various programs as well as constants necessary for calculations, and is arranged such that the contents thereof are read out via the bus 150 by the CPU 100.

A timer 111 is provided to measure lapse of time by counting the number of clock pulses. Thus, the timer 111 supplies the CPU 100 with clock pulses, and also produces an interrupt command signal at a predetermined interval, which is fed to the interrupt control circuit 102.

An output circuit 109 is provided to respectively output drive signals to the fuel injection valves 5. The output circuit 109 comprises a latch, down counter, power transistor so that it produces an output actuating or driving signal in accordance with the results of calculations executed by the CPU 100. The output circuit 109 produces, as the drive signal, a pulse train signal, having a pulse width indicative of fuel injection amount in accordance with fuel amount data obtained by the CPU 100.

A heater control circtui 110 is provided to control the energization of the heater 14a of the oxygen sensor 14 in accordance with the results of calculations executed by the CPU 100. More specifically, the heater 14a is turned on or off in accordance with instructions from the CPU 100. A heater resistance detecting circuit 17 is provided to detect the resistance value RH of the heater 14a and this resistance value RH is inputted to the analog input port 104 to be transmitted to the CPU 100. To detect the resistance value RH, for instance, a predetermined voltage is applied to the heater 14a to detect a current flowing therethrough.

Figure 4:
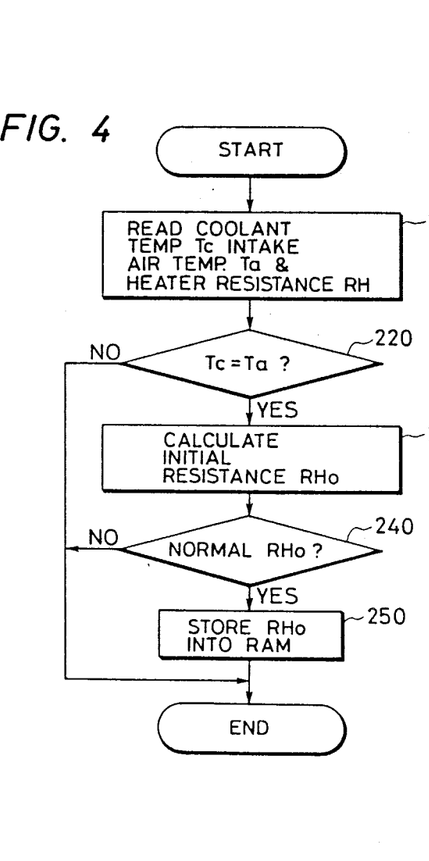
FIGS. 4 and 5 are flowcharts showing the operation of an embodiment of the apparatus.

Now the operation of the control unit 20, especially the CPU 100 thereof, will be described with reference to flowcharts of FIGS. 4 and 5. FIG. 4 illustrates a routine stored in the ROM 108. The control unit 20 is arranged to operate the processing shown in the routine of FIG. 4 and also another proecessing for determining the amount of fuel fed into the cylinders of the engine 1 via the injection valves 5. In FIG. 4, the operational flow of the control unit 20 enters into a step 210 when the key switch 18 is turned on. As soon as the routine is started, initialization is performed to prepare for the following operations with various registers being reset. In addition, the contents of the RAM 107 are checked and necessary resetting is peformed. After this, various engine parameters and other data are read in. In detail, cooltant temperature Tc from the coolant temperature sensor 13, intake air temperature Ta from the intake air temperature sensor 12 and the resistance value RH from the heater resistor detector 17 are all taken via the analog input port 104 into the CPU 100 to store the same into the RAM 107 in a step 210. In a following step 220, it is checked whether the detected coolant temperature Tc equals the detected intake air temperature Ta. If Tc equals Ta, it is regarded that the engine 1 is in completely cooled down state, i.e. engine starting state under a condition in which the heater 14a is in thermally equilibrium with the coolant. In other words, since the fact that the coolant temperature Tc equals the intake air temperature Ta indicates that the engine 1 has not been operated for a long period of time such as several hours, and then the temperature TH of the heater 14a can be regarded to be equal to the coolant or intake air temperature Tc or Ta. In a subsequent step 230, the initial resistance value RHo is calculated using the coolant or intake air temperature Tc or Ta as the temerature TH of the heater 14a and also the temperature coefficient α, which is prestored in the ROM 108, in accordance with the following equation:

$$RHo = RH - \alpha TH$$

As described hereinabove, although the initial resistance value RHo at the absolute zero point is obatained in this embodiment, a resistance value at any other reference value, such as 0° C. may be used in place of such initial resistance value at 0°K. After the initial resistance value RHo is obtained in the step 230, then it is checked whether the obtained RHo is within a given range to determine whether RHo is normal or not. For instance, since an average initial resistance value RHo for a number of oxygen sensors is 0.16 ohm, it is checked whether RHo is within a range from 0.14 to 0.18 ohm. In the case of using 0° C. as the reference temperature, it is checked whether the RHo is within a range from 0.9 to 1.1 ohm. As the above-mentioned temperature coefficient α may be used $3.1 \times 10^{-3}$ ohm/° C. When the initial resistance value RHo is detected to be normal in the step 240, the normal initial reistance value RHo is then stored in the RAM 107 in a following step 250.

In this way, in the embodiment shown in FIG. 4, the initial resistance value RHo of the heater 14a at the time of engine start is calculated to be stored in the RAM 107. Then an interrupt service routine shown in FIG. 5 is executed when an interrupt request occurs. In detail, interrupt request may be produced as a timer interruption from the timer 111 or an engine revolution number interruption from the revolution number counter 101.

Figure 5:
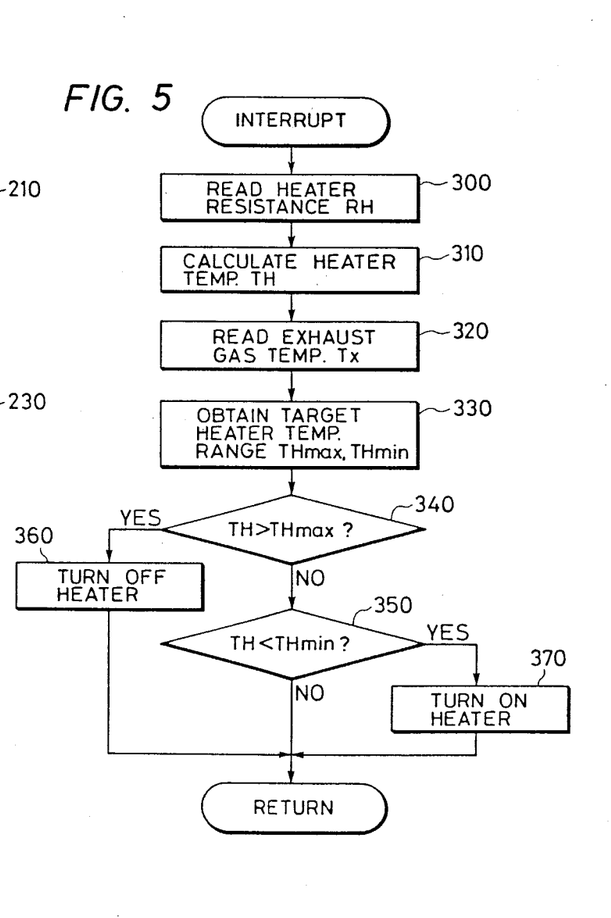

In the interrupt service routine of FIG. 5, the resistance RH of the heater 14a detected by the heater resistance detector 17 is taken into the CPU 100 in a step 300, and then in a following step 310 the temperature TH of the heater 14a is calculated using the following equation:

$$TH = (RH - RHo)/\alpha$$

Figure 6:
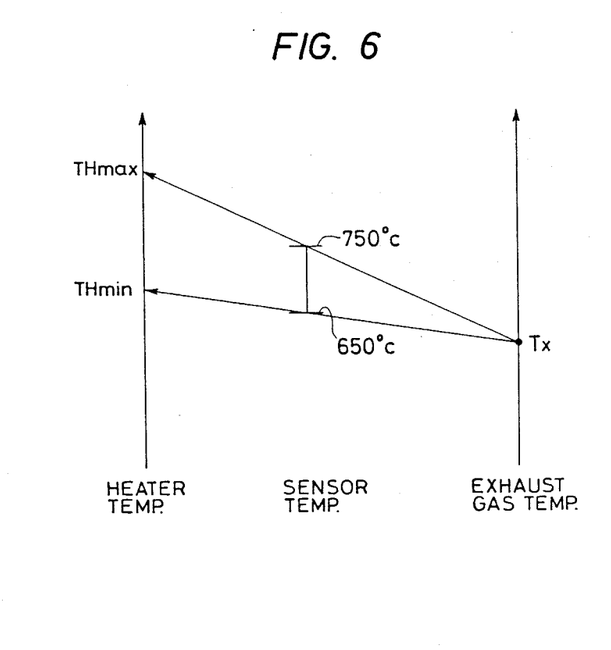
FIG. 6 is a graph useful for understanding the processing shown in a routine of FIG. 5.

As the temperature coefficient α, the above mentioned one prestored in the ROM 108 is used while the above-described initial resistance value RHo obtained and stored in the RAM 107 in the routine of FIG. 4 is used as RHo. In a following step 320, the exhaust gas temperature Tx detected by the exhaust gas temperature sensor 10 is taken into the CPU 100. In the case such exhaust gas temperature sensor 10 is not used, the exhaust gas temperature can be estimated from a data map stored in the ROM 108 using engine rpm and fuel injection amount obtained through another processing routine. Then in a step 330, a target heater temperature range is obtained by calculating an upper limit THmax and an lower limit THmin using the exhaust gas temperature data Tx. This is performed using a given formula or data map. The way of determining the target heater temperature range will be described with reference to FIG. 6. The oxygen sensor 14 has its optimal operating temperature range, such as from 650° C. to 750° C., where this temperature is around electrodes of the sensor 14. Since the heater 14a built in the sensor 14 is spaced apart from the inner electrode, which is closer to the heater 14a than the outer electrode, by a given distance, the temperature TH of the heater 14a should be higher than a desired temperature of the sensor 14. On the other hand, since the exhaust gas temperature sensor 10 is remote from the oxygen sensor 14, the exhaust gas temperature Tx meaured thereby is lower than the temperature of the sensor 14. The above relationship is shown as temperature gradient in FIG. 6. Using the temperature gradient of FIG. 6, once the exhaust gas temperature Tx is obtained, the upper limit THmax and the lower limit THmin of the target temperature range are readily obtained. These upper limit THmax and lower limit THmin are stored in the RAM 107.

Using the upper limit THmax and the temperature TH caclulated in the step 310, it is checked whether TH is higher than the upper limit THmax. If the determination in the step 340 is YES, the heater 14a is turned off in a step 360 to lower the temperature thereof. On the other hand, when the determination in the step 340 is NO, another step 350 is executed to see if TH is lower than the lower limit THmin. If the determination in the step 350 is YES, the heater 14a is turned on in a step 370 to raise the temperature thereof. On the other hand, when the determination in the step 350 is NO, the interrupt service routine is terminated. Similarly, after the execution of the step 360 or 370, the interrupt service routine is terminated. Turning on or off of the heater 14a is performed by sending an instruction signal from the CPU 100 to the heater control circuit 110 used to energize and deenergize the heater 14 in accordance with the instruction signal.

Since the interrupt service routine of FIG. 5 is repeatedly executed at a given interval or at a period corresponding to a given number of engine revolutions, the energization of the heater 14a of the oxygen sensor 14 is controlled such that the temperature TH of the heater 14a is always in the target temperature range which varies in accordance with the exhaust gas temperature Tx. In this way power supply to the heater 14a is controlled such that the temperature of the oxygen sensor 14 is optimal for activating the same. As a result, activation of the oxygen sensor 14 is possible irrespective of the the engine operating condition.

In the above-described embodiment, it is regarded that the temperature TH of the heater 14a equals either the temperature Tc or Ta of the coolant or the intake air as described with the routine of FIG. 4. However, this estimation can be used only when the engine 1 is started after a relatively long time stopping. In the case that the engine is operated for a while so that the temepature TH of the heater 14 is close to the temperature Tx of the exhaust gases, another way of estimation of the temperature TH of the heater 14a may be used.

Figure 7:
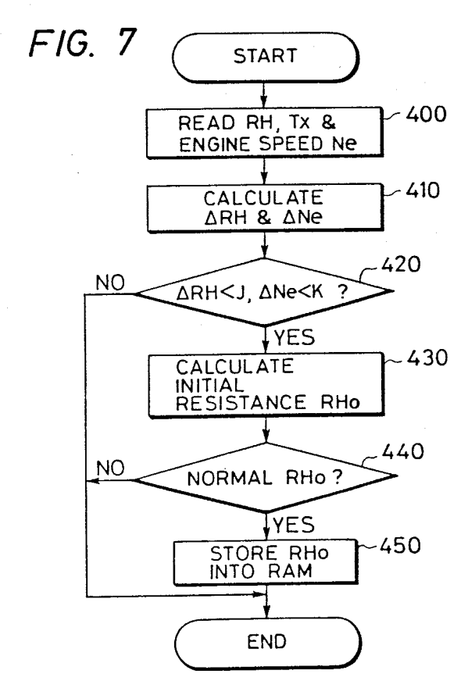
FIG. 7 is a flowchart showing the operation of another embodiment.

Hence, reference is made to FIG. 7 showing a flowchart of a routine for a second embodiment. This routine may be used in place of the routine of FIG. 4. In the routine of FIG. 7, initialization is performed in the same manner as in the first embodiment as described with reference to FIG. 4. Then in a first step 400, various data is taken into the CPU 100 and then stored in the RAM 7. The various data includes engine speed Ne from the revolution number counter 101, exhaust gas temperature Tx from the exhaust gas temperature sensor 10 in addition to the resistance value RH of the heater 14a. Then in a following step 410, the resistance value RH and the engine speed Ne are used to detect their variation ΔRH and ΔNe within a given period of time. To this end the resistance value TH and the engine speed Ne are both measured at least twice respectively in the step 400. In a following step 420, it is checked whether ΔRH is smaller than a predetermined value J or not and whether ΔNe is smaller than a predetemined value K or not. When these two determinations are resulted in YES, it is regarded that the heater 14a exists in thermal equilibrium with the exhaust gases because the temperature of the exhaust gases is constant and the variation in the heater resistance RH is small when the engine 1 is in steady state. Then a step 430 is executed to calculate the initial resistance value RHo using the following equation:

$$RHo = RH - \alpha TH$$

In the above, since actual temperature of the heater 14a is unknown, the exhaust gas temperature Tx or a value close thereto is regarded as the temperature TH of the heater 14a. More specifically, the exhaust gas temperature Tx may be multiplied by a predetermined factor such as value between 1.0 and 1.2.

If the value of ΔRH is larger than the predetermined value therefor, or the value of ΔNe is larger than the predetermined value therefor, then steps 430 to 450 are skipped so that the initial resistance value RHo is not calculated. After the execution of the step 430, steps 440 and 450 which are substantially the same as the steps 240 and 250 of FIG. 4 are executed. Once the value of initial resistance RHo is determined, then on-off control of the heater 14a is performed via the interrupt service routine of FIG. 5 in the same manner as in the first embodiment.

Although the variation in the engine speed Ne is checked in the second embodiment to determine if the engine is in steady state, the variation of the exhaust gas temperature Tx may be checked in place of the engine speed Ne. Therefore, when the exhaust gas temperature Tx is used in place of engine speed Ne, it can be regarded that the heater 14a exists in thermal equilibrium with exhaust gases when the variation of the exhaust gas temperature as well as the variation of the heater resistance RH is small.

From the foregoing, it will be understood that the temerature of the heater of a gas sensor, such as an oxygen sensor, is readily estimated first when the engine is in a particular operating condition, such as a starting state after a relatively long time nonuse or a steady state, and then a resistance value of the heater at a reference temperature such as 0° K. or 0° C. is calculated used the estimated temperature and measured resistance. Once such a reference resistance is obtained, then the temperature of the heater can be readily calculated using a measured resistance value and the known temperature coefficient. In this way, the temperature of the heater is accurately detected so that accurate on-off control in the energization of the heater is possible to keep the sensor in a suitable operating temperature range.

The above-described embodiments are just examples of the present invention, and therefore, it will be apparent for those skilled in the art that many modifications and variations may be made without departing from the scope of the present invention.

What is claimed is:

1. Apparatus for controlling a heater of a gas sensor used for detecting the concentration of a gas component of exhaust gases from an internal combustion engine, comprising:
   (a) a temperature sensor for detecting a temperature relating to said engine;
   (b) first means for detecting a particular engine operating condition of thermal equilibrium from which it is possible to estimate the temperature of said heater using said detected temperature relating to said engine;
   (c) second means for measuring an actual resistance value of said heater;
   (d) third means responsive to said temperature sensor and first and second means for calculating a reference resistance value of said heater at a predetermined reference temperature using said detected temperature relating to said engine and said resistance of said heater at the time said first means detects said particular engine operating condition;
   (e) fourth means responsive to said second and third means for calculating the temperature of said heater using said measured heater resistance value, said reference resistance value obtained by said third means, and a predetermined temperature coefficient and for producing a control signal using the calculated heater temperature so that said calculated heater temperature equals a desired temperature; and
   (f) fifth means for controlling the energization of said heater in accordance with said control signal.

2. Apparatus as claimed in claim 1, wherein said temperature sensor is an engine coolant temperature sensor, and said first means comprises an intake air temperature sensor and means responsive to an output signal from said engine coolant temperature sensor and an output signal from said intake air temperature sensor for determining whether said coolant temperature is equal to said intake air temperature.

3. Apparatus as claimed in claim 1, wherein said temperature sensor is an intake air temperature sensor, and said first means comprises an engine coolant temperature sensor and means responsive to an output signal from said engine coolant temperature sensor and an output signal from said intake air temperature sensor for determining whether said coolant temperature is equal to said intake air temperature.

4. Apparatus as claimed in claim 1, wherein said temperature sensor is an exhaust gas temperature sensor, and said first means comprises means responsive to said second means for determining whether the variation of said actual resistance is smaller than a predetermined value or not, and means for determining whether the variation of the speed of said engine is smaller than a predetermined value or not, said fourth means having means for determining said desired temperature in accordance with an exhaust gas temperature detected by said exhaust gas temperature sensor so as to produce said control signal with which said calculated heater temperature equals said desired temperature.

5. Apparatus as claimed in claim 1, wherein said temperature sensor is an exhaust gas temperature sensor, and said first means comprises means responsive to said second means for determining whether the variation of said actual resistance is smaller than a predetermined value or not, and means for determining whether the variation of said exhaust gas temperature sensor is smaller than a predetermined value or not.

6. Apparatus as claimed in claim 1, wherein said predetermined reference temperature is 0° K.

7. Apparatus as claimed in claim 1, wherein said predetermined reference temperature is 0° C.

8. Apparatus as claimed in claim 1, further comprising an exhaust gas temperature sensor for detecting the temperature of the exhaust gases from said engine, and wherein said fourth means is arranged to obtain a desired temperature range, including said desired temperature, for said heater using said exhaust gas temperature and a desired temperature range for said gas sensor, and to produce said control signal by detecting whether said temperature of said heater obtained using said measured heater resistance is within the desired temperature range for said heater.

9. A method of controlling a heater of a gas sensor used for detecting the concentration of a gas component of exhaust gases from an internal combustion engine, comprising the steps of:
   (a) detecting a temperature relating to said engine;
   (b) detecting a particular engine operating condition of thermal equilibrium from which it is possible to estimate the temperature of said heater using said detected temperature relating to said engine;
   (c) measuring an actual resistance value of said heater;
   (d) calculating a reference resistance value of said heater at a predetermined reference temperature using said temperature relating to said engine and said actual resistance of said heater at the time said particular engine operating condition is detected;
   (e) calculating the temperature of said heater using said measured heater resistance value, said reference resistance value, and a predetermined temperature coefficient;
   (f) producing a control signal using the calculated heater temperature so that said calculated heater temperature equals a desired temperature; and
   (g) controlling the energization of said heater in accordance with said control signal.

10. A method as claimed in claim 9, wherein said temperature relating to said engine is the engine coolant temperature, and said particular engine operating condition is detected when said coolant temperature is equal to intake air temperature of said engine.

11. A method as claimed in claim 9, wherein said temperature relating to said engine is engine intake air temperature, and said particular engine operating condition is detected when said intake air temperature is equal to coolant temperature of said engine.

12. A method as claimed in claim 9, wherein said temperature relating to said engine is engine exhaust gas temperature, and said particular engine operating condition is detected when the variation of said actual resistance is smaller than a predetermined value, and when the variation of engine speed is smaller than a predetermined value.

13. A method as claimed in claim 9, wherein said temperature relating to said engine is engine exhaust gas temperature, and said particular engine operating condition is detected when the variation of said actual resistance is smaller than a predetermined value, and when the variation of said exhaust gas temperature is smaller than a predetermined value.

14. A method as claimed in claim 9, further comprising the steps of:
(a) detecting the temperature of the exhaust gases from said engine; and
(b) obtaining a desired temperature range, including said desired temperature, for said heater using said exhaust gas temperature so that said control signal is produced by detecting whether said temperature of said heater obtained by said heater resistance value is within the desired temperature range for said heater.

* * * * *